United States Patent [19]

Olivier

[11] Patent Number: 5,574,118
[45] Date of Patent: *Nov. 12, 1996

[54] OLEFIN POLYMERS CONTAINING BOUND ANTIOXIDANT

[75] Inventor: Errol J. Olivier, Baton Rouge, La.

[73] Assignee: DSM Copolymer, Inc., Baton Rouge, La.

[*] Notice: The term of this patent shall not extend beyond the expiration date of Pat. No. 5,017,727.

[21] Appl. No.: 398,930

[22] Filed: Mar. 6, 1995

Related U.S. Application Data

[63] Continuation of Ser. No. 245,808, May 17, 1994, abandoned, which is a continuation of Ser. No. 120,639, Sep. 13, 1993, abandoned, which is a continuation of Ser. No. 7,653, Jan. 22, 1993, abandoned, which is a continuation of Ser. No. 608,292, Nov. 2, 1990, abandoned.

[51] Int. Cl.⁶ .................................................. C08F 232/04
[52] U.S. Cl. .......................... 526/281; 526/160; 524/392
[58] Field of Search ................................ 526/281, 160; 524/392; 568/67

[56] References Cited

U.S. PATENT DOCUMENTS

| | | | |
|---|---|---|---|
| 2,050,843 | 4/1933 | Jacobsohn | 524/96 |
| 4,017,669 | 4/1977 | Collette et al. | 526/169 |
| 4,301,306 | 11/1981 | Layer | 568/734 |
| 5,017,727 | 5/1991 | Olivier | 568/719 |

FOREIGN PATENT DOCUMENTS 1278516  6/1992  United Kingdom.

*Primary Examiner*—Mark Nagumo
*Attorney, Agent, or Firm*—Rockey, Rifken and Ryther

[57] ABSTRACT

This invention is addressed to olefin polymers having antioxidant properties which are prepared by Ziegler polymerization of one or more monomers containing ethylenic unsaturation along with a polymerizable antioxidant monomer in the form of a substituted norbornene in which at least one substituent contains one or more groups imparting to the molecule antioxidant properties.

38 Claims, No Drawings

OLEFIN POLYMERS CONTAINING BOUND ANTIOXIDANT

This is a continuation of application Ser. No. 08/245,808 filed on May 17, 1994 abandoned which is a continuation of Ser. No. 08/120,639 filed Sep. 13, 1993 which is a continuation of Ser. No. 08/007,653 filed Jan. 22, 1993, now abandoned, which is a continuation of Ser. No. 07/608,292 filed Nov. 2, 1990, now abandoned.

BACKGROUND OF THE INVENTION

This invention relates to olefin polymers possessing antioxidant properties prepared by Ziegler polymerization of the polymerizable antioxidant monomer with alpha-olefins. This invention further provides a method of introducing functionality into polyolefins by direct Ziegler catalysis without excessive use of co-catalyst or blocking agents.

The development of the now well known Ziegler catalyst system has made it possible to polymerize alpha-olefins to highly useful polymers and copolymers. One of the principal drawbacks to the Ziegler catalyst system is that it cannot be used with monomers containing functional groups which are polar in nature. As a general rule, such polar functional groups have a tendency to react irreversibly with components of the Ziegler catalyst system, thereby lowering the true concentration of the Ziegler catalyst components.

Equally well known is the fact that virtually all polyolefins require stabilization against uncontrolled oxidation which has a tendency to cause undesirable changes in the polymer, including chain scission, cross-linking and discoloration, and thus, adversely change the mechanical and physical properties of the polymer. Extensive search has been undertaken in the area of stabilization, and that research has resulted in the development of a number of antioxidants which impart greater stability to olefin polymers, including elastomeric olefin polymers. A major class of antioxidants which has been developed over the years is the class of hindered phenols.

While molecular antioxidants such as the hindered phenols have achieved wide spread use in the stabilization of a wide variety of polyolefins, they have a tendency under certain conditions of use to migrate out of the polymer which results in the depletion of the antioxidant in the polymer, and consequently the polymer has a tendency to be degraded through oxidation. The use of bound antioxidants which remain in the polymer under conditions which promote the migration of molecular antioxidants has been advocated by (1) Kline, R. H. and Miller, J. P., "Preparation and Activity of Polymerizable Antioxidants for Emulsion Rubbers," *Rubber Chemistry and Technology*, 46, 96 (1973); (2) Meyer, G. E., Kavchok, R. W. and Naples, F. J., "Emulsion Rubbers Copolymerized with Monomeric Antioxidants," *Rubber Chemistry and Technology*, 46, 106 (1973); (3) Horvath, J. W., "Bound Antioxidant Stabilized NBR in Automotive Applications," *Elastomerics*, August, 1979, page 19; (4) Kuczkowski, J. A. and Gillick, J. G., "Polymer-Bound Antioxidants," *Rubber Chemistry and Technology*, 57, 621 (1984); (5) Engels, H. W. et al., "Effectiveness of New Alkyl-Aryl-p-Phenylenediamines Which Can Be Chemically Bound to Polymers - Model Study," *Rubber Chemistry and Technology*, 62, 609 (1989); (6) Parker, D. K. and Schulz, G. O., "N-(4-Anilinophenyl)-Methacrylamide, A Polymerizable Amine Antioxidant: Synthesis, Copolymerization, Copolymer Properties, and Performance," *Rubber Chemistry and Technology*, 62, 732 (1989); (7) Gandek, T. P., Hatton, T. A. and Reid, R. C., "Batch Extraction with Reaction: Phenolic Antioxidant Migration from Polyolefins to Water. 2. Experimental Results and Discussion," *Ind. Eng. Chem. Res.*, 28, 1036 (1989); and (8) Miller, D. E. et al., "Persistent Antioxidants for Polymers Contacting Extractive Media," *Rubber World*, August 1989, page 13. Such antioxidants are characterized as polymer-bound by reason of the fact that they are chemically attached to the polymer either by way of a grafting reaction or by copolymerization with the olefinic monomers during the production of the polymer itself.

Polymer-bound antioxidants which result from copolymerization with the other monomers have been generally limited to free radical polymerizations, and particularly the free radical emulsion copolymerization of butadiene and acrylonitrile in the production of NBR rubbers. Typical polymer-bound antioxidant monomers include amide or ester derivatives of acrylic or methacrylic acid which can be copolymerized by way of a free radical mechanism with the butadiene and acrylonitrile. While such polymer-bound antioxidants are well suited as monomers in free radical polymerization techniques, they are unsuitable for use in polymerizations catalyzed by the Ziegler catalyst system because their polar groups tend to act as catalyst poisons.

It has been proposed in U.S. Pat. Nos. 3,748,316; 3,796,687 and 4,017,669 to incorporate by copolymerization polar monomers using a Ziegler catalyst system. Specifically, those prior patents suggest certain norbornene compounds having a phenolic group chemically bound thereto as monomers for copolymerization with ethylene and propylene by way of a Ziegler catalyst system. The general teachings of those references include a compound said to have the following general structure:

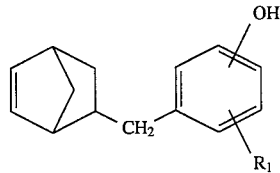

where $R_1$ is either R or OR and R can be alkyl, aryl or cycloalkyl containing 1–18 carbon atoms or hydrogen.

The teachings of the three patents do not describe any technique by which compounds of that type can be prepared, nor do they describe a polymerization with such a monomer. Therefore, the three patents fail to place those compounds and copolymers prepared therefrom in the possession of the public. Additionally, it is also important to note that these patents overcome the poisoning effect of polar groups by using an equal molar quantity of aluminum alkyl to polar monomer (not the monomer referred to herein), a very expensive solution, as well as impractical in view of environmental and purity standards of today's rubber and plastics industry. Furthermore, no recognition is given to the potential for the phenolic type polar monomer to impart antioxidant properties to the polar copolymer obtained therefrom.

U.S. Pat. No. 4,301,306 describes norbornenyl monophenolic compounds of the general structure below:

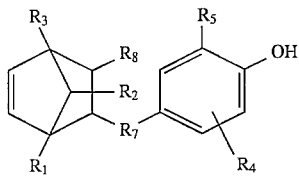

as having a reactive double bond and thereby being polymerizable. This patent teaches neither how to use the reactive norbornenyl phenolic compound in polymerization reactions, nor does it demonstrate that once polymerized, the copolymer thus obtained possesses antioxidant properties.

Norbornenyl monophenolic compounds described above were the subject of U.S. Pat. No. 4,355,148 where a ring opening polymerization using a metathesis catalyst produced a polymeric antioxidant composition incorporating the norbornenyl phenolic compound with dicyclopentadiene, norbornene or substituted norbornenes, and optionally an olefin such as 1-hexane.

It is accordingly an object of the present invention to provide polyolefins possessing antioxidant properties prepared by conventional Ziegler polymerization processes whereby the olefin-containing antioxidant is copolymerized with the alpha-olefin or mixture of olefins, and is directly incorporated into the polymer backbone. A further object of the invention is to introduce functionality into the polyolefins by direct Ziegler catalysis without use of special techniques such as blocking groups and excessive use of organoaluminum co-catalyst.

The concepts of the invention reside in Ziegler-polymerizable antioxidant compounds which are in the form of a substituted norbornene in which the substituent contains one or more groups imparting to the molecule antioxidant properties. Preferred among the antioxidant-imparting substituent are hindered hydroxy-substituted aromatic groups, the most preferred being hindered alkyl-substituted phenols.

In a preferred embodiment, the Ziegler-polymerizable antioxidants of the present invention are compounds having the general formula:

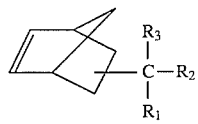

wherein $R_1$ is an antioxidant-imparting substituents having the formula:

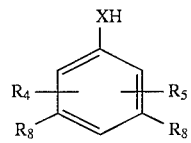

and $R_2$ is either a hydrogen atom, a group having the definition set forth in $R_1$, or the formula below:

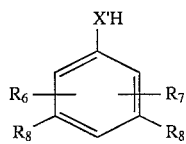

In each of the formulas, X and X' are selected from a divalent oxygen atom and/or a divalent sulfur atom; $R_4$, $R_5$, $R_6$, and $R_7$ are each independently alkyl containing 1–8 carbon atoms such as methyl, ethyl, propyl, isopropyl, butyl, t-butyl, pentyl, isopentyl, etc. or additionally $R_4$ and $R_6$ can be hydrogen, $R_8$ is either hydrogen, methyl, ethyl, or mixtures thereof, and $R_3$, in the above structure, is either hydrogen or alkyl containing 1–4 carbon atoms such as methyl, ethyl, propyl, etc. The composition of these Ziegler polymerizable antioxidants are the subject of co-pending U.S. patent application Ser. No. 550,373 filed Jul. 10, 1990, now U.S. Pat. No. 5,017,727 the disclosure of which is incorporated herein by reference.

A suitable route for synthesis of the monophenolic olefin containing antioxidants of the present invention is disclosed in Layer U.S. Pat. No. 4,301,306 and is incorporated herein by reference. Layer uses the well known Diels Alder reaction to form a 2-norbornene substituted in the 5-position with an alkylene or alkenylene phenolic group by reacting a cyclopentadiene with a 4-alkenyl phenol as shown below:

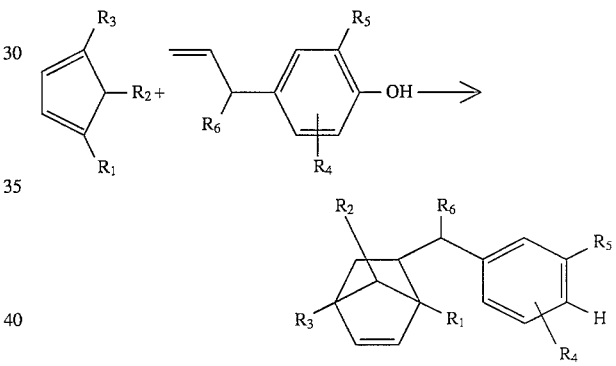

Specific preferred examples would include the following structures:

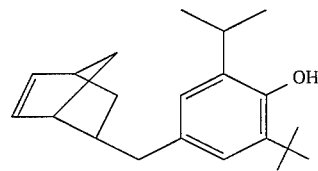

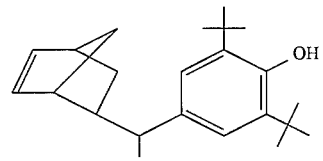

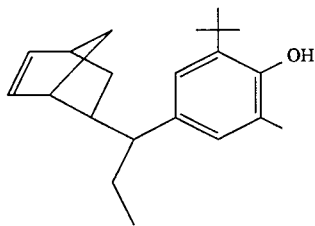

Preferred among the foregoing norbornene bisphenolics are the following compounds:

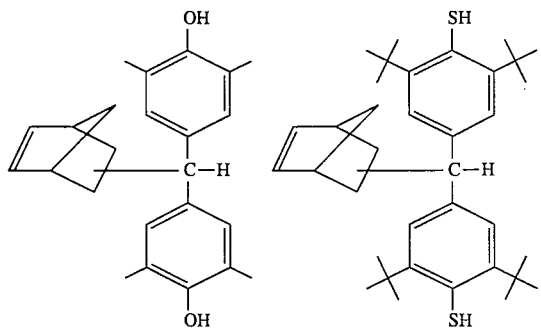

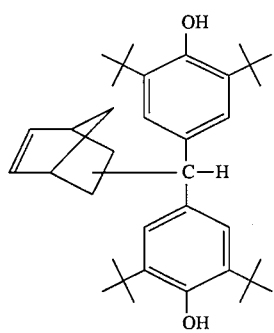

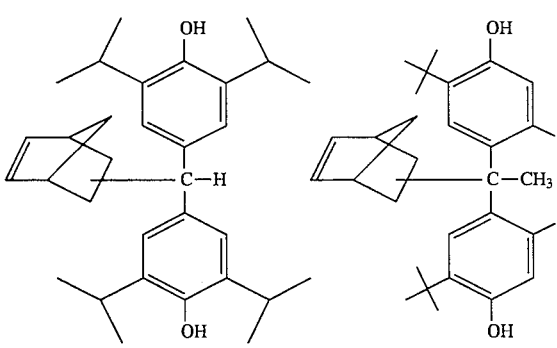

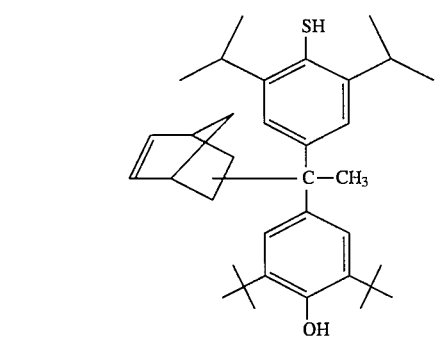

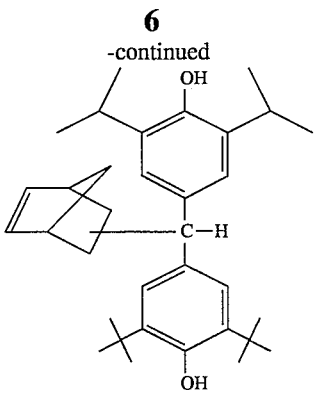

The bisphenolic polymerizable antioxidants of the present invention are prepared by the base catalyzed condensation reaction of a disubstituted phenol and/or a disubstituted thiophenol with a 2-norbornene carboxy compound as shown by the following equation:

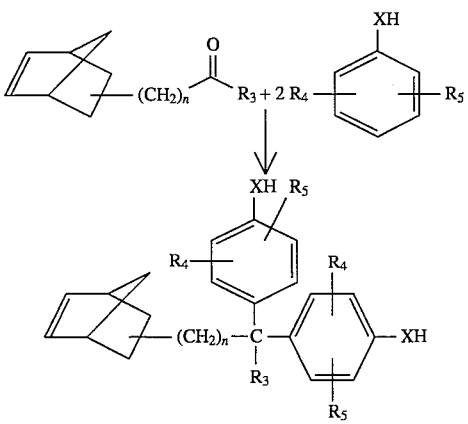

Suitable 2-norbornene carboxy compound would include those where $R_3$ is hydrogen or an alkyl group such as methyl, ethyl, propyl, etc. with the carboxy substitution occurring at any location on the norbornene ring except the double bonded carbons. Beta,gamma-unsaturated norbornenones such as the structures below:

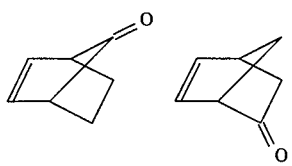

would also be suitable starting materials for the condensation reaction with phenols or thiophenols to yield polymerizable antioxidants of the following structures:

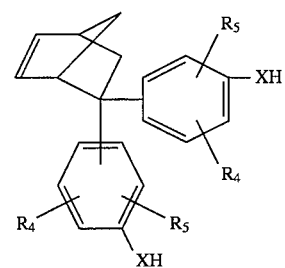

-continued

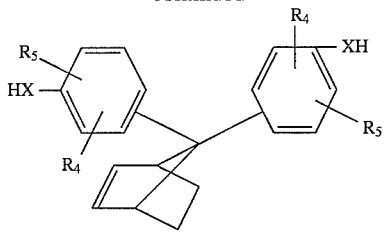

Disubstituted phenols and/or disubstituted thiophenols appropriate for practice of this invention would have $R_4$ and $R_5$ groups each independently alkyl containing 1–8 carbon atoms such as methyl, ethyl, propyl, isopropyl, butyl, t-butyl, pentyl, isopentyl, etc.

The specific product from the reaction between 2-norbornene-5-carboxaldehyde and two equivalents of 2,6-di-tert-butylphenol has been designated Bisphenol N and is shown as follows:

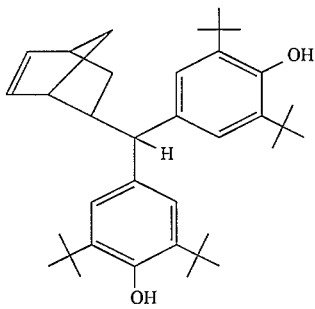

In the case in which two different phenolic and/or thiophenolic groups are substituted on the same norbornene molecule, the corresponding polymerizable antioxidant can be prepared by using an appropriate mixture, typically an equimolar mixture of the two phenols, thiophenols or mixture of phenol with thiophenol to form the corresponding mixed product.

The reaction is carried out by dissolving the phenol or thiophenol in a lower alkanol solvent such as methyl alcohol followed by the addition of potassium hydroxide in the dissolved state. Then the 2-norbornene-5-carboxaldehyde is added, followed by neutralization and recovery of the desired compound or mixture of compounds.

As will be appreciated by those skilled in the art, if use is made of a mixture of phenols, a mixture of thiophenols or a mixture of phenol with a thiophenol, then the product will likely be a mixture of compounds in which the norbornene molecule is substituted with mixed phenols and thiophenols.

The Ziegler polymerizable antioxidants of the present invention find particular utility as co-monomers in the Ziegler catalyzed polymerization of olefins, generally. Thus, the polymerizable antioxidant of the present invention can be copolymerized with any alpha-olefin such as ethylene, propylene, butene or hexene with conjugated or non-conjugated dienes such as butadiene, isoprenes and 1,4-hexadiene and with styrene. In addition, the antioxidants of the present invention can be used as co-monomers in the polymerization of olefin mixtures to produce terpolymers, tetrapolymer, etc. The resultant antioxidant- containing polymers can be crystalline or amorphous and find utility broadly, in applications from plastics to elastomerics.

Typical Ziegler catalysts useful in the practice of this invention are comprised of a transition metal compound in which the metal is selected from Group IV—VI of the Periodic Table (as published in *CRC Handbook of Chemistry and Physics*, by The Chemical Rubber Company, Cleveland, Ohio) used in combination with a base metal alkyl or hydride with at least one carbon to metal bonded group and the metal selected from Group I-III of the Periodic Table. Examples of commonly employed transition metals would include vanadium, titanium, zirconium, cobalt, chromium and nickel. Examples of base metal alkyls commonly used are various organo aluminum compounds, organo aluminum halides, organo zinc compounds or organo magnesium compounds. The transition metal component may be homogeneous or heterogeneous and can be complexed with or used in combination with an electron donating chemicals such as organic esters, amines, phosphines, silicates or others. Alternately, the transition metal can be supported on an inert carrier such as MgO, $MgCl_2$, silica or alumina. Also suitable in the practice of this invention, particularly for preparation of antioxidant bound polyethylenes, is $CrO_3$ supported on activated silica-alumina, also known as the "Phillips catalyst."

The Ziegler polymerization reaction with the olefin containing antioxidant monomer is not process limited and can be carried out in solution, slurry, gas phase or any combination of such processes. The choice of process, as known to those skilled in the art, will depend on the type of polyolefin and the specific Ziegler catalyst system.

The active Ziegler catalyst is not adversely effected by the polymerizable antioxidant monomer. Standard Ziegler polymerization techniques, including those for molecular weight control known to those skilled in the art, can be utilized to obtain polymers with bound antioxidant at the same predetermined molecular weight, molecular weight distribution, stereo-specificity and co-monomer levels as for standard polymers. The molar ratio of catalyst components, that is base metal alkyl to transition metal component is unchanged. Also the procedure for addition of the catalyst components need not be altered. No pre-reaction of the base metal alkyl with the polymerizable antioxidant monomer is required, nor is one desired.

A useful example of Ziegler polymerization of the antioxidant of the present invention with a mixture of alpha-olefins is in the preparation of EPM rubbers and in the terpolymerization of ethylene, an alpha-olefin containing 3–18 carbon atoms, and a non-conjugated diene as in the preparation of EPDM rubbers. Suitable dienes in the preparation of such EPDM polymers include 1,4-hexadiene, monocyclic polyenes and polycyclic polyenes. Representative of such compounds include dicyclopentadiene, octadienes, cyclo-(2,2,1)-hepta-2,5-diene, the alkylidene norbornenes wherein the alkylidene group contains 1 to 20 carbon atoms and preferably 1 to 8 carbon atoms, the alkenyl norbornenes, and particularly the 5-alkenyl-2-norbornenes wherein the alkenyl group contains about 3 to 20 carbon atoms. Other suitable bridged ring polyenes include polyunsaturated derivatives of bicyclo-(2,2,2)-hexane such as bicyclo-(3,2,1)hexane, polyunsaturated derivatives of bicyclo-(3,3,1) -nonane and polyunsaturated derivatives of bicyclo-(3,2,2) -nonane.

Examples of preferred bridged ring compounds include 5-methylene-2-norbornene, 5-ethylidene-2-norbornene, 5-vinyl-2-norbornene, 5-n-propylidene-2-norbornene, 5-isobutylidene-2-norbornene, 5-n-butylidene-2-norbornene, dicyclopentadiene, 5-(2-methyl-2-butenyl)-2-norbornene, 5-(3-methyl-2-butenyl) -2-norbornene and 5-(3,5-dimethyl-4-hexenyl) -2-norbornene.

The EPM/EPDM rubbers incorporating the polymerizable antioxidants of the present invention in the polymer backbone contain molar ratios of ethylene to propylene (or other of the $C_3$ to $C_{16}$ mono-olefins) varying between 95:1 to 5:90 of ethylene: propylene, and preferably between 85:15 to 55:45 of ethylene: propylene. The polyene or substituted polyene is chemically bound in the EPDM rubber in an amount within the range of 0 to 30 weight percent. The polymerizable antioxidant monomer of the present invention is bound into the polyolefin backbone in an amount ranging from 0.001 to 20 weight percent, depending in part on the particular use to which the polymer is put. The same amount of polymerizable antioxidant can be used in the other polymers as outlined above.

Such polymers are produced in an interpolymerization in the presence of a Ziegler-catalyst well known to those skilled in the art. The techniques for producing such EPM or EPDM interpolymers is well known and is described in U.S. Pat. Nos. 2,933,480, 3,093,621, 3,211,709, 3,646,168, 3,790,519, 3,884,993, 3,894,999 and 4,059,654, as well as many others.

The polymerizable antioxidant monomers described herein are also usefully employed in copolymerization with ethylene to produce high density polyethylene, including ultra high molecular weight polyethylene and with ethylene and alpha-olefins such as butene, hexene and octene to produce linear low density polyethylene. The reaction is carried out in accordance with standard conditions known to those skilled in the art with polymerizable antioxidant monomer being added as a solution of hexane, toluene, liquid monomer or aliphatic hydrocarbons.

Copolymerization of the polymerizable antioxidant monomers of the present invention with propylene or with propylene/alpha-olefin mixtures at a level of 0.01–1.0 weight percent produces thermoplastic propylene polymers resistant to auto-oxidation, and thereby capable of being processed under less restrictive conditions compared to conventional polypropylene type thermoplastics.

The polymerizable antioxidant of the present invention is thus copolymerized with the alpha olefin or mixtures of alpha olefins and serves to impart antioxidant properties to the polymer. One of the advantages of the present invention is that unlike antioxidants which are physically blended with a polymeric composition and have a tendency to migrate through the polymer matrix, the polymerizable antioxidants of the present invention do not undergo such migration because they are chemically bonded to the polymer matrix. The tendency to extract or leach out the antioxidant from fabricated articles where there is fluid contact during end use would also be overcome by practice of this invention. Incorporation of 0.1 to 2.0 weight percent polymerizable antioxidant monomer into the polyolefin backbone results in oxidative stability during isolation, transport and storage. Incorporation of levels of 0.5 to 20 weight percent polymerizable antioxidant monomer into the polyolefin backbone will provide oxidative stability for high temperature processing of the polyolefin. At these high levels of copolymerized antioxidant, the polyolefin will also be useful for blending with polyolefins and/or polymers not possessing antioxidant properties.

Having described the basic concepts of the invention, reference is now made to the following examples, which are provided by way of illustration and not by way of limitation, of the practice of the present invention in the preparation of the polymerizable antioxidants of the invention and their use in the interpolymerization with various monomers.

EXAMPLE 1

This example illustrates the preparation and characterization of the condensation product of 2,6-di-t-butylphenol with 2-norbornene-5-carboxaldehyde to yield a product which has been designated Bisphenol N (BPN).

Synthesis of Bisphenol N

The reaction is carried out in a 500 ml 3-neck flask equipped with a mechanical stirrer, addition funnel, condenser and heating mantle. The flask was charged the 100 ml reagent methanol containing 5.2 grams dissolved KOH representing 0.08 moles of KOH. This is followed by 41.2 grams (0.2 moles) of 2,6-di-tert-butylphenol. The mixture is placed under nitrogen, warmed gently, and stirred until the phenol dissolves. A solution of 9.8 grams (0.08 moles) of 5-norbornene-2-carboxaldehyde (mixture of isomers) in 20 ml methanol is added dropwise through the addition funnel with stirring. The reaction mixture is heated at the reflux temperature for 16 hours, after which it is allowed to cool to room temperature. A precipitate forms, which can be collected by filtration and washed with fresh methanol. The product is a white powder having a melting point of 203 to 205° C. A yield of 20.0 grams, representing 48 percent of the theoretical yield, is obtained.

Characterization of Bisphenol N.

Bisphenol N is a colorless crystalline solid having a melting point of 204 to 205° C. The IR spectrum of Bisphenol N exhibits the following absorptions:

| Frequence ($cm^{-1}$) | Relative Abundance | Assignment |
| --- | --- | --- |
| 3660 | med-strong | phenolic O—H |
| 3070 | weak | Olefinic/aromatic CH |
| 2980 | strong | Aliphatic C—H |
| 1560 | weak | C=C |

Peaks in the mass spectrum (solids probe, 70 eV) are listed below:

| Mass | Frequency | Assignment |
| --- | --- | --- |
| 516 | 25% | Molecular ion |
| 423 | 100% | Loss of norbornenyl radical |
| 297 | 10% | Loss of one phenol group |
| 219 | 11% | Tropylium-type ion |
| 93 | 24% | Norbornenyl ion |
| 57 | 98%% | t-Butyl ion |

The proton and $^{13}C$ NMR spectra of Bisphenol N are consistent with the assigned structure. The NMR data indicate that BPN is a mixture of exo and endo isomers. This is supported by liquid chromatography analysis.

Elemental analysis: Anal. Calcd. for $C_{36}H_{52}O_2$; C,83.65: H,10.16;0,6.19 Found: C,83.85; H,10.16;0,5.99 (by difference)

EXAMPLE 2

This example illustrates the interpolymerization of Bisphenol N with ethylene and propylene.

In a typical polymerization, 2.0 ml of a solution of 4.09 g recrystallized Bisphenol N in 8.61 g toluene was added to a Sutherland batch reactor containing 3.8 millimoles ethyl aluminum sesquichloride, 0.4 millimoles vanadyl chloride, 0.3 millimoles pyridine and 0.05 millimoles butyl perchlorovinylacetate in 900 ml hexane and copolymerized with ethylene and propylene. The reactor temperature was 38° C.

and the total pressure on the reactor was 30 psig. The reactor pressure was maintained throughout the run by adding a mixture of 60 percent ethylene and 40 percent propylene. After 20 minutes, the reaction was stopped by killing the catalyst with 1.0 ml isopropyl alcohol and the polymer produced (19.0 grams) was precipitated by adding the reaction mixture to isopropyl alcohol.

The polymer produced in Example 2 was extracted with cyclohexane and acetone to remove any residual monomer and then was examined by means of infrared spectroscopy. The presence of Bisphenol N is indicated by the hydroxyl absorption band at 3610 cm$^{-1}$.

EXAMPLE 3

This example provides the general procedure used for the interpolymerization of ethylene, propylene and ethylidene norbornene.

A pop bottle was filled with 150 ml hexane, 0.8 millimole ethyl aluminum sesquichloride, 0.065 millimole vanadyl chloride, 0.02 millimole butyl perchlorovinylacetate, 0.3 grams ethylidene norbornene and 0.05 millimole pyridine. The reaction pressure was maintained at 30 psig by adding a mixture of 60 percent ethylene and 40 percent propylene. The reaction was carried out at room temperature and stopped after 20 minutes by the addition of isopropyl alcohol.

The following examples illustrate the interpolymerization of Bisphenol N with ethylene, propylene and ethylidene norbornene.

EXAMPLE 4 to 8

Polymerizations were carried out as described in Example 3 with the addition of various amounts of Bisphenol N as 30 percent solution in toluene. The weight of the total reaction mixture was determined after the run, and the solution analyzed for residual Bisphenol N by high pressure liquid chromatography. The results are shown in Table I.

During the course of the chromatographic analysis, it was noticed that the standard solutions of the Bisphenol N monomer exhibited two peaks which may be related to two isomers of Bisphenol N. The ratio of these two peaks in the starting material ranged from 1.05 to 1.09. The higher ratio in the residual Bisphenol N after polymerization may indicate that the two isomers polymerize at different rates.

TABLE 1

| | | Residual Bisphenol N After Polymerization | | | |
|---|---|---|---|---|---|
| | | | Bisphenol N | | Residual |
| Example | Polymer Grams | Added mg | Residual ppm | Wt. % Bound In Polymer | Monomer Isomer Ratio |
| 4 | 2.70 | 0 | 0 | 0 | — |
| 5 | 2.41 | 20 | 10 | 0.78 | 1.49 |
| 6 | 2.46 | 40 | 20 | 1.54 | 1.61 |
| 7 | 2.35 | 80 | 55 | 3.22 | 1.52 |
| 8 | 2.74 | 160 | 100 | 5.43 | 1.46 |

The data in Table I shows that polymer yield and catalyst mileage are not adversely effected by increasing levels of Bisphenol N in the polymerization medium. In each example, 5–7, the percent conversion of Bisphenol N was approximately 90–95, behavior similar to that of ethylidene norbornene in that the percent copolymerized is independent of concentration.

EXAMPLE 9A

This example provides the general procedure used for synthesis of an analog of Bisphenol N, alpha,alpha-bis(2,6-dimethylphenol)-5-methylene- 2 -norbornene.

The reaction was carried out in a 200 ml three neck roundbottom flask equipped with a condenser, mechanical stirrer and rubber septum. The flask was charged with 50 ml reagent methanol, 5.2 grams (0.08 mole) KOH pellets and 24.4 grams (0.2 mole) 2,6-dimethylphenol. A nitrogen atmosphere was set up by admitting nitrogen through the septum and letting it exit through the condenser via a bubbler containing mineral oil. 5-Norbornene-2-carboxaldehyde (9.8 grams, 0.08 moles) was added via syringe through the septum. The reaction mixture was heated at the reflux temperature with stirring for sixteen hours. Upon cooling, the product remained in solution. The solution was neutralized with 4 molar HCl to pH 5–7. The mixture was diluted with 100 ml dichloromethane. This was washed three times in a separatory funnel with 30 ml portions of fresh water. The solution was dried over magnesium sulfate. After filtration to remove the drying agent, the solution was evaporated to provide 27.5 grams of a solid residue. This was purified by column chromatography (silica gel, 1/1 hexane/ dichloromethane) to yield 16.5 grams of product representing a 59 percent yield. Recrystallization from toluene provided colorless crystals which had a melting point of 176° to 178° C. This product is the Bisphenol N analog having methyl groups substituted on the phenol rings in place of the t-butyl groups.

EXAMPLE 9B

Polymerization of an EPDM with alpha,alphabis (2,6-dimethylphenol)-5-methylene-2-norbornene A Sutherland batch reactor was charged with 900 ml dry hexane purged with nitrogen and propylene to remove all traces of oxygen and pressurized to 10 psig with propylene. An additional 20 psig of a 60 percent ethylene/40 percent propylene mixture was added to give a total reactor pressure of 30 psig.

To this reactor were added 4.8 millimoles of ethyl aluminum sesquichloride, 0.3 millimoles of pyridine, 0.15 millimoles of butyl perchlorovinylacetate, 0.192 grams of the dimethyl analog of Bisphenol N added as a solution in toluene and 0.05 millimoles of vanadyl trichloride. The reaction temperature was 40° C. and the reactor pressure was maintained at 30 psig throughout the run by the continuous addition of the 60 percent ethylene feed. The run was terminated after 20 minutes by the addition of 1.0 ml of isopropanol. The polymer was coagulated in isopropanol and dried in a vacuum oven.

A total of 5.8 grams of polymer was produced. It had a reduced solution viscosity of 2.08. The polymer contained 65.1 weight percent ethylene and 0.79 weight percent alpha, alpha bis(2,6-dimethylphenol)-5-methylene-2-norbornene as determined by infrared analysis.

EXAMPLE 10

Propylene Polymerization with Bisphenol N by a Titanium Catalyst

A Sutherland batch reactor was charged with 500 ml of dry hexane and purged with nitrogen, then propylene to remove all traces of oxygen. Diethylaluminum chloride, 5.4 mole, in hexane were added to the reactor and the temperature increased to 60° C. The reactor was then charged with 0.18 g of Bisphenol N in hexane and 2.7 mmole of titanium trichloride catalyst. The reactor pressure was immediately increased to 30 psig with propylene and maintained there by continuous feeding of propylene. After one hour, the reaction was terminated by addition of 10 ml of methanol. Crystalline polypropylene, 24 grams, was recovered by filtration after the hexane slurry was twice extracted with 400 ml of water. Infrared analysis on the oven-dried polypropylene showed incorporation of 0.3 weight percent Bisphenol N.

EXAMPLE 11A–E

The following examples illustrate the interpolymerization of Bisphenol N with ethylene and propylene.

Polymers were prepared as in Example 3 except that no ethylidene norbornene was used. No residual Bisphenol N was observed in the solution after completion of the polymerization reaction. The polymers were recovered by coagulation with isopropanol, dried at room temperature under vacuum and used as standards for an analytical method based on the infrared absorption band at 3610 cm$^{-1}$. The results are shown in Table II:

TABLE II

| Example | Polymer grams | Added mg | Wt. % Bound in Polymer |
|---|---|---|---|
| 11A | 4.29 | 0 | 0 |
| 11B | 4.55 | 2.4 | 0.05 |
| 11C | 4.18 | 6 | 0.14 |
| 11D | 3.75 | 12 | 0.32 |
| 11E | 4.05 | 24 | 0.59 |

EXAMPLES 12 and 13

The following examples 12A–E and 13A–F compare polymerization of ethylene, propylene and Bisphenol N in toluene and ethylidene norbornene as solvent.

EXAMPLES 12A–E

Polymers were prepared according to the procedure of Example 2, except that 0.2 millimoles of vanadyl chloride and 0.1 millmoles of butyl perchlorovinylacetate were used. Bisphenol N was added as a solution of 0.6 grams Bisphenol N in 25 ml toluene. The results are shown in Table III:

TABLE III

| Bisphenol N in Toluene Solution | | |
|---|---|---|
| Example | Bisphenol N mg Added | Polymer Yield grams |
| 12A | 12 | 15.4 |
| 12B | 24 | 14.6 |
| 12C | 48 | 16.2 |
| 12D | 0 | 16.2 |
| 12E | 0 | 15.4 |

Since Bisphenol N is a solid at room temperature, it is convenient to add it to the polymerization reactor as a solution in an inert solvent. Although toluene is an excellent solvent for Bisphenol N, other solvents may be used. In general, any solvent could be used which does not contain polar groups that would poison the catalyst. A particularly useful solvent for introducing Bisphenol N into EPDM reactors is ethylidene norbornene, since it is already added as a co-monomer.

EXAMPLES 13A–E

Polymers were prepared according to the procedure of Example 2 except that Bisphenol N was added as a solution of 1 gram of Bisphenol N in 25 ml ethylidene norbornene. Additional ethylidene norbornene was added so that the total amount of ethylidene norbornene was 1.0 grams. The results are shown in Table IV:

TABLE IV

| Bisphenol N in Ethylidene Norbornene Solution | | |
|---|---|---|
| Example | Bisphenol N mg Added | Polymer Yield grams |
| 13A | 12 | 8.7 |
| 13B | 24 | 10.6 |
| 13C | 48 | 12.7 |
| 13D | 0 | 13.1 |
| 13E | 0 | 13.6 |

EXAMPLE 14

Polyethylene Copolymer with Bisphenol N Prepared with Vanadium Catalyst

A Sutherland reactor was charged with 900 ml of dry hexane and 0.16 g of Bisphenol N, then purged several times to remove traces of oxygen and pressurized to 26 psig with ethylene. Hydrogen (4 psig) was added to control molecular weight. The reactor was heated to 40° C. and the catalyst components added in the sequence listed: 4.8 millimoles ethyl aluminum sesquichloride, 0.12 millimoles butyl perchlorovinylacetate and 0.02 millimoles vanadyl trichloride. Ethylene was added continuously throughout the reaction to maintain the reactor pressure at 30 psig. After 20 minutes, 1.0 ml isopropanol was added to stop the reaction. The polymer produced (7.6 g) was recovered, and then twice dissolved in trichlorobenzene and reprecipitated before being analyzed by infrared spectroscopy for the presence of hindered phenolic groups. The infrared analysis showed that the polyethylene contained 0.64 phr Bisphenol N.

EXAMPLE 15

Antioxidant Bound Polyethylene Prepared With Titanium Catalyst

EXAMPLE 15A (Polyethylene)

Polyethylene may also be produced using titanium catalysts. A Sutherland reactor was charged with 900 ml of dry hexane, purged several times to remove traces of oxygen and pressurized to 30 psig with ethylene. The reactor was heated to 40° C. and 6.0 millimoles diethyl aluminum chloride and 1.8 millimoles beta-titanium trichloride were added. Ethylene was added continuously throughout the reaction to maintain the reaction pressure at 30 psig. After 20 minutes, 1.0 ml isopropanol was added to stop the reaction. The polymer produced (17 g) was oven-dried to remove residual solvent.

EXAMPLE 15B (with Bisphenol N)

Polyethylene was produced by the same method as in Example A except that 0.096 g of Bisphenol N was also added. The polymer produced (9.3 g) was recovered and reprecipitated before being analyzed by infrared spectroscopy for the presence of hindered phenolic groups. The infrared analysis showed that the polyethylene contained 0.33 weight percent Bisphenol N.

EXAMPLE 16–21

Oven Aging Study of Polymers Containing BPN

The following examples illustrate oven aging of EPM copolymers containing Bisphenol N.

Samples of EPM and EPDM containing either admixed or copolymerized BPN were prepared and tested for resistance to oven aging at 100° C. in a forced air oven. Samples containing admixed Irganox® 1076, a commercial antioxidant made by Ciba-Geigy, and samples free of antioxidant were used as controls. EPM samples were monitored by RSV. EPDM samples were monitored by measuring gel formation. The results of the oven aging studies are listed in Tables V and VI.

Control Example 16A

A Sutherland batch reactor was carefully purged with nitrogen and filled with 900 ml of dry hexane. The reactor was purged again with nitrogen and propylene and pressurized to 30 psig at 40° C. with a gas mixture of 60 percent ethylene and 40 percent propylene. Ethyl aluminum sesquichloride (4.8 millimole), pyridine (0.3 millimole), butyl perchlorovinylacetate (0.2 millimole) and vanadyl chloride (0.1 millimole) were added to the reactor. The reaction was killed after 20 minutes by the addition of 1.0 ml of isopropanol and the polymer recovered and dried. The product was an ethylene/propylene copolymer having an RSV of 1.9 and an ethylene content of 57 mole percent.

Control Example 16B

The polymer of Control Example 16A was dissolved in hexane. Bisphenol N (0.35 phr) was added to the solution. The rubber was recovered by coagulation in acetone.

Control Example 16C

The polymer of Control Example 16A was dissolved in hexane. Bisphenol N (0.35 phr) was added to the solution. The rubber was recovered by evaporation of the hexane.

Control Example 16D

The polymer of Control Example 16A was dissolved in hexane. Irganox 1076 (0.35 phr) was added to the solution. The rubber was recovered by evaporation of the hexane.

Control Example 17A

This polymer was prepared in the same manner as in Example 16A but 1.0 gram of ethylidene norbornene was also added to the reactor. The product was an ethylene/propylene/ethylidene norbornene terpolymer having an RSV of 2.1, an ethylene/propylene molar ratio of 65:35 and an ethylidene norbornene content of 4.6 weight percent.

Control Example 17B

The polymer of Control Example 17A was dissolved in hexane. Bisphenol N (0.2 phr) was added to the solution. The rubber was recovered by acetone coagulation.

Control Example 17C

The polymer of Control Example 17A was dissolved in hexane. Bisphenol N (0.2 phr) was added to the solution. The rubber was recovered by evaporation of the hexane.

Control Example 17D

The polymer of Control Example 17A was dissolved in hexane. Irganox 1076 (0.2 phr) was added to the solution. The rubber was recovered by evaporation of the hexane.

EXAMPLES 18 and 19

These polymers were prepared in the same manner as in Example 16 but Bisphenol N was added during polymerization as a solution of 0.6 g Bisphenol N in 25 ml toluene. Different amounts of solution were added to give 0.2 weight percent Bisphenol N in Example 18 and 0.35 weight percent Bisphenol N in Example 19. The products were ethylene/propylene/Bisphenol N terpolymers whose properties are listed in Table V along with the properties of Control Examples 16A–D. Prior to oven aging, these. samples were dissolved in hexane and coagulated with acetone.

EXAMPLES 20 and 21

These polymers were prepared in the same manner as in Example 17, but Bisphenol N was added as a solution of Bisphenol N in ethylidene norbornene. Different amounts of solution were added to give 0.1 weight percent Bisphenol N in Example 20 and 0.2 weight percent Bisphenol N in Example 21. Enough additional ethylidene norbornene was added to each so that the total amount of ethylidene norbornene added in each was 1.0 gram. The products were ethylene/propylene/ethylidene norbornene/Bisphenol N tetrapolymers whose properties are listed in Table VI along with the properties of Control Examples 17A–D. Prior to oven aging, these samples were dissolved in hexane and coagulated with acetone.

The results in Tables V and VI demonstrate that the polymerizable antioxidant Bisphenol N in its copolymerized form performs as well as admixed antioxidants (co-BPN polymers vs C and D controls), after ten weeks at 100° C., with the added advantage of providing resistance to extraction or migration (co-BPN polymers vs A and B controls). A comparison of the A and B controls illustrates that acetone coagulation removes unbound antioxidant. Copolymerized BPN is not removed by acetone coagulation.

TABLE V

Oven Aging Study of E/P/BPN Terpolymers

| Example | 16A | 16B | 18 | 19 | 16C | 16D |
|---|---|---|---|---|---|---|
| % BPN | 0 | 0.35 | 0.2 | 0.35 | 0 | 0 |
| % Irganox 1076 | 0 | 0 | 0 | 0 | 0 | 0.35 |
| Method of Incorporation | — | Admixed | Copl'zd | Copl'zd | Admixed | Admixed |
| Recovery | Evap | Acetone Coag'd | Acetone Coag'd | Acetone Coag'd | Evap | Evap |
| RSV* | | | | | | |
| Initial | 1.9 | 1.9 | 2.1 | 2.0 | 1.9 | 1.9 |
| Week 2 | 0.8 | 0.9 | 2.0 | 1.8 | 1.9 | 1.9 |
| Week 4 | 0.1 | 0.2 | 2.1 | 2.5 | 1.6 | 1.3 |
| Week 6 | — | — | 2.1 | 2.3 | 1.8 | 1.9 |
| Week 8 | — | — | 2.1 | 2.4 | 1.7 | 2.2 |
| Week 10 | — | — | 1.9 | 2.5 | 1.8 | 2.0 |

*RSV is Reduced Solution Viscosity measured at 135° C. on a 0.1 (W/V) percent solution in decalin.

TABLE VI

Oven Aging Study of E/P/EN/BPN Tetrapolymers

| Examples | 17A | 17B | 20 | 21 | 17C | 17D |
|---|---|---|---|---|---|---|
| RSV | 2.3 | 2.3 | 2.1 | 2.6 | 2.3 | 2.1 |
| Wt. % EN | 4.6 | 4.6 | 4.6 | 4.0 | 4.6 | 3.9 |
| % BPN | 0 | 0.2 | 0.1 | 0.2 | 0.2 | 0 |
| % Irganox 1076 | 0 | 0 | 0 | 0 | 0 | 0.2 |
| Method of Incorporation | — | Admixed | Copl'zd | Copl'zd | Admixed | Admixed |
| Recovery | Evap | Acetone Coag'd | Acetone Coag'd | Acetone Coag'd | Evap | Evap |
| % Gel* | | | | | | |
| Initial | 0.5 | 0.5 | 2.3 | 0 | 0.5 | 0 |
| Week 2 | 83.0 | 73.0 | 0 | 1.4 | 0 | 0 |
| Week 4 | — | — | 0 | 0 | 0 | 0 |
| Week 6 | — | — | 1.7 | 0 | 1.7 | 0 |
| Week 8 | — | — | 3.4 | 4.3 | 3.5 | 3.4 |
| Week 10 | — | — | 4.9 | 6.7 | 3.5 | 3.4 |

*Gel % is the percent insoluble in toluene measured at room temperature on a 1(W/V) percent solution.

EXAMPLES 22–23

Effect of Reaction Variables On Bisphenol N Incorporation

Bisphenol N does not appear to act as a catalyst poison. This can be seen from the preceding examples 4–8 where 0.78–5.4 weight percent of Bisphenol N copolymerized in an EPDM recipe had little effect on the amount of polymer produced. However, all of these examples were prepared under similar conditions, so further experimentation was carried out to see if the same conclusions could be drawn at different levels of promotor and/or at different monomer concentrations.

EXAMPLES 22A–D

Polymers were prepared in the same manner as in Examples 16 and 17, except that different levels of the promoter, butyl perchlorovinylacetate (PCVAE), were used. Larger amounts of Bisphenol N were also used at two different levels. The results are shown in Table VII.

TABLE VII

Effect of Promoter Level on Polymerization

| | | | | Bisphenol N | | |
|---|---|---|---|---|---|---|
| Example | PCVAE mmole | Polymer Yield Grams | Mileage g/mmole | mg Added | Wt. % Bound in Polymers | RSV |
| 22A | 0.2 | 21.3 | 213 | 160 | 0.44 | 2.20 |
| 22B | 0.4 | 33.1 | 331 | 160 | 0.27 | 2.02 |
| 22C | 0.2 | 18.0 | 180 | 320 | 0.97 | 2.00 |
| 22D | 0.4 | 28.4 | 284 | 320 | 0.64 | 1.99 |

There appears to be a slight reduction in catalyst mileage at higher levels of Bisphenol N. This slight reduction in mileage can be overcome by increasing the concentration of promoter.

EXAMPLES 23A–D

Polymers were prepared in the same manner as in Examples 32–33, except that 0.6 millimole of butyl perchlorovinylacetate promoter was used and the reactor feed was composed of 80 percent ethylene and 20 percent propylene. Hydrogen was also added to the feed at conventional levels to regulate molecular weight.

TABLE VIII

Bisphenol N Polymerization with 80% Ethylene Feed

| Example | Hydrogen psig | Polymer Yield grams | Mileage g/mmole | Bisphenol N mg Added | Bisphenol N Wt. % Bound In Polymer |
|---|---|---|---|---|---|
| 23A | 4 | 58.6 | 586 | 320 | 0.36 |
| 23B | 8 | 66.3 | 663 | 320 | 0.40 |
| 23C | 4 | 66.2 | 662 | 160 | 0.25 |
| 23D | 8 | 64.3 | 643 | 160 | 0.28 |

The effect of hydrogen appears to be typical for the catalyst system employed regardless of the amount of Bisphenol N. There also is little effect on polymer chemical characteristics as measured by reduced solution viscosity or gel permeation chromatography.

TABLE IX

Polymer Molecular Weight Distributions

| Example | RSV | $M_n$ | $M_w$ | $M_w/M_n$ |
|---|---|---|---|---|
| 23A | 1.76 | $4.36 \times 10^4$ | $1.01 \times 10^5$ | 2.31 |
| 23B | 1.38 | $3.95 \times 10^4$ | $0.83 \times 10^5$ | 2.35 |
| 23C | 1.79 | $5.11 \times 10^4$ | $1.20 \times 10^5$ | 2.35 |
| 23D | 1.42 | $3.87 \times 10^4$ | $0.81 \times 10^5$ | 2.09 |

EXAMPLE 24

Continuous Polymerization with Bisphenol N

Reactions were carried out in a 4-liter glass reactor with a stainless steel top equipped with openings for addition of desired components, a dip tube for removal of polymerization liquid, an agitator blade to provide mixing and an internal coil to provide cooling. The continuous polymerization was carried out at a temperature of 33° C. and a pressure of 33 psig with temperature control maintained by the rate of circulation of cool water through the cooling coil and pressure controlled by the rate of catalyst addition. Hexane, monomers and other components were added continuously to the reactor while the polymerization liquid was removed at a continuous rate to maintain a constant liquid level in the reactor.

Feed rates to the reactor included hexane at 4.72 liters/hour, propylene at 3.20 standard liters per minute, ethylene at 1.90 standard liters per minute, hydrogen at 17 cc/minute (3.5 mole % in V.S.) and ammonia at 1.12 cc/minute (0.50 mM/l). Dilute solutions of ethylaluminumsesquichloride, vanadium oxytrichloride and butyl percholorocrotonate in hexane were added as separate streams at feed rates of 10.0, 0.50 and 0.60 mM/hour respectively. Ethylidene norbornene was added at a feed rate of 11.2 g/hour diluted in hexane. The BPN feed rate was 0 in run A, 3.2 g/hour in run B and 6.1 g/hour in run C. BPN was added dissolved in EN solution.

A continuous vent stream (of 450 cc/minute) was removed from the reactor vapor space to provide a sample for the on-line G.C. and to prevent build-up of inert gas in the reactor.

The discharge of polymerization solution from the reactor was continuously deactivated and washed with water in a second agitated vessel. The polymer production rate resulting from this polymerization procedure was 200 g/hour. Polymer was recovered from the polymerization solution by steam stripping and the resulting polymer was dried in a hot air oven at 50°–60° C. for 40 hours. Irganox 1076 type antioxidant was added to the washed reactor solution before stream stripping on run A. No Irganox 1076 was added to runs B and C. The results are shown in Table X.

TABLE X

Continuous Polymerization with BPN

| | A | B | C |
|---|---|---|---|
| BPN g/hr., feed | 0 | 3.2 | 6.1 |
| EN g/hr., feed | 11.2 | 11.2 | 11.2 |
| Polymer Analysis | | | |
| ML 1 + 4 @ 257° F. | 79 | 82 | 81 |
| RSV | 2.75 | 2.75 | 2.73 |
| Mole % $C_2$ | 65.5 | 68.4 | 69.3 |
| EN, C=C/1000° C. | 5.36 | 5.09 | 5.16 |
| BPN, wt. % | 0 | 1.96 | 2.65 |

EXAMPLE 25

Polymerization of an EPDM with alpha-(2,6-di-tert-butylphenol)-5-methylene-2-norbornene Using the same general procedure described in Example 9B, alpha-(2,6-di-tert-butylphenol) -5-methylene-2-norbornene is copolymerized with ethylene and propylene. The polymer can contain about 0.84 weight percent of the polymerizable antioxidant.

It will be understood that various changes and modifications can be made in the details of procedure, formulations and use without departing from the spirit of the invention, especially in the following claims:

I claim:

1. A polyolefin prepared by Ziegler polymerization of an olefin selected from the group consisting of an alpha-olefin, a diene, a mixture of alpha-olefins, and a mixture of alpha-olefins and a diene or polyene with a polymerizable antioxidant monomer having the formula:

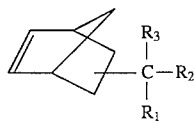

wherein $R_1$ is an antioxidant-imparting substituent having the formula:

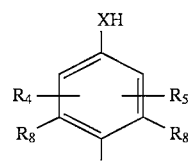

and $R_2$ is either a hydrogen atom, a group having the definition set forth in $R_1$ or the formula below:

21

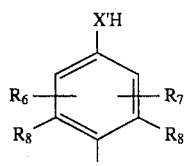

wherein each X and X' is selected from the group consisting of a divalent oxygen atom and a divalent sulfur atom; and $R_4$ and $R_6$ are each independently alkyl containing 1–8 carbon atoms or hydrogen, $R_5$ and $R_7$ are alkyl containing 1–8 carbon atoms, $R_8$ is either hydrogen, methyl, ethyl or mixtures thereof, and $R_3$ is either hydrogen or an alkyl containing 1–4 carbon atoms, wherein the polymerization is carried out in the presence of a Ziegler catalyst and no prereaction between the polymerizable antioxidant monomer and the Ziegler catalyst is effected.

2. A polyolefin as defined in claim 1 wherein the olefin is ethylene.

3. A polyolefin as defined in claim 1 wherein the olefin is propylene.

4. A polyolefin as defined in claim 1 wherein the olefin is butene.

5. A polyolefin as defined in claim 1 wherein the olefin is ethylene and propylene.

6. A polyolefin as defined in claim 1 wherein the olefin is ethylene and $C_3$–$C_{10}$ alpha-olefins.

7. A polyolefin as defined in claim 1 wherein the olefin is ethylene, propylene and at least one polyene.

8. A polyolefin as defined in claim 1 wherein the olefin is propylene and $C_4$–$C_{10}$ alpha-olefins.

9. A polyolefin as defined in claim 1 wherein the olefin is propylene and one or more dienes.

10. A polyolefin as defined in claim 1 wherein the olefin is isoprene.

11. A polyolefin as defined in claim 1 wherein the olefin is butadiene.

12. A polyolefin as defined in claim 1 wherein the olefin is 4-methyl-1-pentene.

13. A polyolefin as defined in claim 1 wherein X is oxygen.

14. A polyolefin as defined in claim 1 wherein $R_2$ is hydrogen.

15. A polyolefin as defined in claim 1 wherein $R_4$ and $R_5$ are alkyl groups in positions ortho to the XH group.

16. A polyolefin as defined in claim 1 wherein one of X and X' is sulfur.

17. A polyolefin as defined in claim 1 wherein the antioxidant monomer is Bisphenol-N.

18. A polyolefin as defined in claim 1 wherein the antioxidant monomer has the formula:

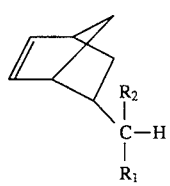

22 and $R_1$ and $R_2$ have the formula:

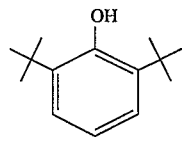

and are attached to the 5-methylene carbon at positions ortho or para to the phenol group.

19. A polyolefin as defined in claim 1 wherein the antioxidant monomer is bound to the olefin polymer in an amount ranging from 0.001 to 20 percent by weight.

20. A process for polymerization of antioxidant bound polyolefins comprising contacting in the presence of a Ziegler catalyst (1) an olefin selected from the group consisting of an alpha-olefin, a mixture of alpha-olefins, a diene, and a mixture of alpha-olefins and a diene or polyene with (2) a polymerizable antioxidant monomer having the formula:

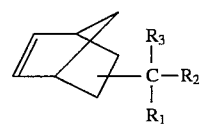

wherein $R_1$ is an antioxidant-imparting substituent having the formula:

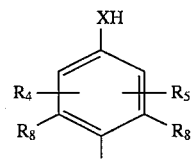

and $R_2$ is either a hydrogen atom, a group having the definition set forth in $R_1$ or the formula below:

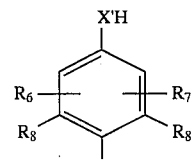

wherein each X and X' is selected from the group consisting of a divalent oxygen atom and a divalent sulfur atom; and $R_4$ and $R_6$ are each independently alkyl containing 1–8 carbon atoms or hydrogen, $R_5$ and $R_7$ are alkyl containing 1–8 carbon atoms, $R_8$ is either hydrogen, methyl, ethyl or mixtures thereof, and $R_3$ is either hydrogen or an alkyl containing 1–4 carbon atoms, wherein no prereaction between the polymerizable antioxidant monomer and the Ziegler catalyst is effected.

21. A process as defined in claim 20 wherein the olefin is ethylene.

22. A process as defined in claim 20 wherein the olefin is propylene.

23. A process as defined in claim 20 wherein the olefin is butene.

24. A process as defined in claim 20 wherein the olefin is ethylene and propylene.

25. A process as defined in claim 20 wherein the olefin is ethylene and $C_3$–$C_{10}$ alpha-olefins.

26. A process as defined in claim 20 wherein the olefin is ethylene, propylene and at least one polyene.

27. A process as defined in claim 20 wherein the olefin is propylene and $C_4$–$C_{10}$ alpha-olefins.

28. A process as defined in claim 20 wherein the olefin is propylene and one or more dienes.

29. A process as defined in claim 20 wherein the olefin is isoprene.

30. A process as defined in claim 20 wherein the olefin is butadiene.

31. A process as defined in claim 20 wherein the olefin is 4-methyl-1-pentene.

32. A process as defined in claim 20 wherein X is oxygen.

33. A process as defined in claim 20 wherein $R_2$ is hydrogen.

34. A process as defined in claim 20 wherein $R_4$ and $R_5$ are alkyl groups in positions ortho to the XH group.

35. A process as defined in claim 20 wherein one of X and X' is sulfur.

36. A process as defined in claim 20 wherein the antioxidant monomer is Bisphenol-N.

37. A process as defined in claim 20 wherein the antioxidant monomer has the formula:

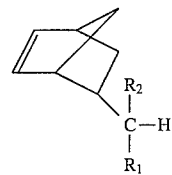

and $R_1$ and $R_2$ have the formula:

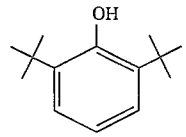

and are attached to the 5-methylene carbon at positions ortho or para to the phenol group.

38. A process as defined in claim 20 wherein the antioxidant monomer is bound to the olefin polymer in an amount ranging from 0.001 to 20 percent by weight.

* * * * *